(12) United States Patent
Gündel

(10) Patent No.: US 8,467,586 B2
(45) Date of Patent: Jun. 18, 2013

(54) METHOD AND APPARATUS FOR REGISTERING TOMOGRAPHIC VOLUME DATA RECORDS OF THE INTESTINE

(75) Inventor: Lutz Gündel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 684 days.

(21) Appl. No.: 12/585,866

(22) Filed: Sep. 28, 2009

(65) Prior Publication Data
US 2010/0080435 A1    Apr. 1, 2010

(30) Foreign Application Priority Data
Sep. 29, 2008   (DE) .......................... 10 2008 049 467

(51) Int. Cl.
*G06K 9/00*   (2006.01)

(52) U.S. Cl.
USPC .......................................... 382/131; 382/128

(58) Field of Classification Search
USPC .............................. 382/128, 131; 378/4, 98.12
See application file for complete search history.

(56) References Cited

U.S. PATENT DOCUMENTS

| | | | |
|---|---|---|---|
| 4,644,582 A * | 2/1987 | Morishita et al. | 382/130 |
| 5,647,360 A * | 7/1997 | Bani-Hashemi et al. | 600/425 |
| 5,848,121 A * | 12/1998 | Gupta et al. | 378/62 |
| 6,009,212 A * | 12/1999 | Miller et al. | 382/294 |
| 6,154,518 A * | 11/2000 | Gupta | 378/62 |
| 6,181,832 B1 * | 1/2001 | Maas, III | 382/294 |
| 6,526,117 B1 * | 2/2003 | Okerlund et al. | 378/8 |
| 6,738,063 B2 * | 5/2004 | Shen et al. | 345/424 |
| 6,754,374 B1 * | 6/2004 | Miller et al. | 382/128 |
| 6,771,736 B2 * | 8/2004 | Sabol et al. | 378/98.12 |
| 6,816,572 B2 * | 11/2004 | Jabri et al. | 378/98.9 |
| 6,865,249 B2 * | 3/2005 | Mehldau | 378/8 |
| 6,879,711 B2 * | 4/2005 | Maurincomme et al. | 382/128 |
| 7,127,093 B2 * | 10/2006 | Bansal et al. | 382/128 |
| 7,231,076 B2 * | 6/2007 | Fu et al. | 382/131 |
| 7,450,780 B2 * | 11/2008 | Roche et al. | 382/276 |
| 7,778,490 B2 * | 8/2010 | Quist | 382/294 |
| 8,265,354 B2 * | 9/2012 | Zhang et al. | 382/128 |
| 2004/0136584 A1 * | 7/2004 | Acar et al. | 382/131 |
| 2005/0048456 A1 * | 3/2005 | Chefd'hotel et al. | 434/267 |
| 2005/0163356 A1 * | 7/2005 | Makram-Ebeid et al. | 382/128 |
| 2007/0122016 A1 | 5/2007 | Brejl et al. | |
| 2008/0118111 A1 | 5/2008 | Sirohey et al. | |

FOREIGN PATENT DOCUMENTS

| | | |
|---|---|---|
| DE | 102006054822 A1 | 5/2007 |
| DE | 102007052857 A1 | 5/2008 |

* cited by examiner

*Primary Examiner* — Alexander H Taningco
(74) *Attorney, Agent, or Firm* — Harness, Dickey & Pierce, P.L.C.

(57) ABSTRACT

A method and an apparatus are disclosed for registering volume data records of the intestine which were recorded in different positions of a patient. In at least one embodiment of the method, an approximate registration is firstly performed on the basis of central lines. In a subsequent detailed registration, the approximate registration is refined on the basis of local anatomical features in the intestine, for example by using the profile of folds and/or the distance of intestinal sections from fixed points of the intestine. At least one embodiment of the method and/or the apparatus permit a more accurate registration of the at least two volume data records.

20 Claims, 3 Drawing Sheets

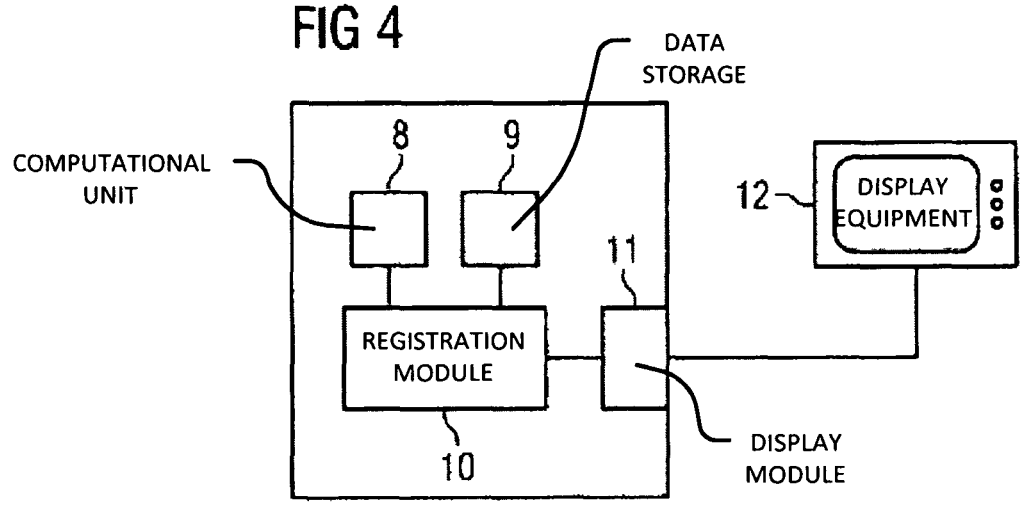

METHOD AND APPARATUS FOR REGISTERING TOMOGRAPHIC VOLUME DATA RECORDS OF THE INTESTINE

PRIORITY STATEMENT

The present application hereby claims priority under 35 U.S.C. §119 on German patent application number DE 10 2008 049 467.4 filed Sep. 29, 2008, the entire contents of which are hereby incorporated herein by reference.

FIELD

At least one embodiment of the present invention generally relates to a method and/or an apparatus for registering at least two volume data records of the intestine which were recorded in two different positions of a patient using a tomographic imaging method. In at least one embodiment of the method, a registration matrix is generated which assigns to each voxel illustrating the intestine in the one volume data record a corresponding voxel in the other volume data record which is intended to represent the same location in the intestine.

BACKGROUND

In the search for lesions in the large intestine or other regions of the intestine, volume data records from slice image methods, such as computed tomography or magnetic resonance imaging, are utilized. In this case, a volume data record is understood to be a 3D image data record. During the tomographic imaging, the intestine is filled with a suitable contrast agent and can be segmented from the data record. Subsequently it is visualized for the user by means of a suitable visualization technique, for example by using multiplanar reformatting (MPR) or by way of a virtual flight.

However, in the clinical routine, the intestine is often not filled completely with the contrast agent during the image recording. The sections of the intestine which are not filled are collapsed and cannot be examined. If a lesion is located there, it is not recognized during the recording and displaying of only one image data record. This problem is generally avoided by recording two tomographic volume data records in two different positions of the patient, usually in the prone and dorsal positions. Here the assumption is made that the contrast agent is differently distributed when the patient is repositioned, different intestinal sections are contrasted or collapsed, and 100% of the intestinal surface is visible and can be examined when observed over both data records.

During this procedure, the user is required to be able to navigate from a particular position in the image of the intestine of the one patient position to the identical position in the image of the other patient position. This requires that the two image or volume data records are registered. Using the registration matrix generated during the registration, the corresponding image voxel in the other volume data record can then be found for every image voxel in the one volume data record.

Recording the tomographic volume data records in different positions of the patient is also advantageous in that residual stool remaining in the intestine can be distinguished from possible lesions. Despite patient preparation using medication, such residual stool stays in the intestine and can lead to an erroneous diagnosis if only one volume data record is used. Residual stool does not adhere to the intestinal wall in most cases but follows the gravitational pull and therefore always lies on the bottom side of the intestinal tube in any patient position. It is for this reason that in the case of suspicious structures in one patient position, the corresponding position in the other patient position is always examined in the respective volume data records. If the structure of interest follows the gravitational pull when the patient is repositioned, it does not adhere to the intestinal wall and therefore the possibility of a lesion can be ruled out. The registration of the two volume data records in this case also permits quick comparison of the identical position in the intestine in the two volume data records.

Until now, such volume data records of the intestine have been registered on the basis of so-called central lines. These central lines can be middle lines of the segmented intestine, lines according to the "longest view" method or flight paths in the intestine generated automatically or by the user. In any case these central lines follow the profile of the intestine in the respective image data records. Then similarities are determined between the central lines of the image data records to be registered, in particular of the prone and dorsal positions of the patient, and are used to calculate the registration matrix. However, for many regions of the intestine the registration matrix determined in this manner is only imprecise. This is because the intestine only has three fixed points in the body but can otherwise, particularly after the repositioning, be at different positions in the abdominal cavity. When navigating in the image data records on the basis of such a registration matrix it is therefore only possible to navigate in each case to the vicinity of the desired position when switching from one image data record to the other.

SUMMARY

In at least one embodiment of the present invention, a method and an apparatus are specified for registering two volume data records of the intestine and which obtain a more precise registration.

In at least one embodiment, the proposed method and the associated apparatus permit precise registration and displaying of at least two volume data records of the intestine, particularly the large intestine, which were recorded in two different positions of a patient using a tomographic imaging method. By way of example, the two different positions can be the prone and dorsal positions. In at least one embodiment of the method, a registration matrix is generated which assigns to each voxel illustrating the intestine in the one volume data record a corresponding voxel in the other volume data record which is intended to represent the same location in the intestine. So as to generate the registration matrix, an approximate registration is firstly performed in which an intestinal profile is respectively determined for the two volume data records and the two volume data records are registered on the basis of similarities between the two intestinal profiles. This approximate registration can be effected using the known registration methods on the basis of central lines, as described briefly in the introductory part of the description. Subsequent to the approximate registration, the present method then performs a detailed registration in which the present approximate registration is refined on the basis of local anatomical features in the intestine so as to obtain the registration matrix.

A substantially more precise registration matrix is obtained by the detailed registration which follows the approximate registration. The method of at least one embodiment thus permits the user to exactly navigate to the respectively corresponding positions in the intestine in addition to a fast switch between the two volume data records.

In at least one embodiment of the proposed method and at least one embodiment of the associated apparatus, the volume data records can include a number of assembled individual slice images or can be directly obtained from the imaging equipment as volume data records. Computed tomography and magnetic resonance imaging are mainly used as tomographic imaging methods. However, it goes without saying that at least one embodiment of the method can also be obtained using other tomographic image data records, e.g. from ultrasound imaging, positron emission tomography (PET) or SPECT (single photon emission computed tomography). The image data contained in the volume data records in each case represents individual volume elements of the examined region and is referred to as a voxel.

So as to perform the detailed registration, different local anatomical features of the intestine can be used. In one refinement of the method and the apparatus, the fixed points of the intestine are determined and assigned for this purpose in the two volume data records. The respectively same intestinal sections are then determined in the two volume data records by means of their (identical) distance along the respective intestinal profile from the fixed points. To this end, one, two or all three fixed points of the intestine can be used. The three fixed points of the intestine are the rectum and the two flexures. In this refinement, the assumption is made that only the position of the intestine in the abdomen varies when the patient is repositioned but not the length of the intestine between the individual intestinal sections and the fixed points. Regions of the intestine which have the same distance from the respective fixed point in the two image data records should therefore correspond to the same region of the intestine and be used to refine the approximate registration.

This refinement can be effected by firstly the generation of a provisional registration matrix using the approximate registration, which registration matrix is then adjusted or corrected on the basis of the additional data from the detailed registration.

As an alternative or in addition to using the fixed points, intestinal folds and/or the profile of the longitudinal muscles of the intestine are also advantageously used to refine the registration. In one refinement, the folds in the intestine are detected for individual or all intestinal sections in respectively one of the volume data records and then folds of similar size and shape are sought after in the vicinity of the corresponding region in the other image data record obtained from the approximate registration. The assumption is then made that the found folds of similar size and shape correspond to the same position in the intestine. This information is used to refine the approximate registration. The shape and size of the folds can be detected automatically using known pattern recognition methods. However, user interaction, in which the user determines the respectively similar structures visually, is also possible.

The profile of the longitudinal muscles in the volume data records can also be determined and compared in similar fashion so as to be used for the detailed registration. It goes without saying that a combination with the previously described refinements is also possible.

In a further refinement of at least one embodiment, the vertices of the folds are determined for the respective intestinal sections in a rendered display in each case one of the volume data records and connected for each fold by lines which run through the valleys between the vertices caused by the longitudinal muscles. Corresponding lines are drawn in the other image data record in the vicinity of the corresponding region obtained by the approximate registration. Subsequently, lines of a similar shape to those in the first image data record are sought after in this other image data record so as to refine the registration.

In a further refinement, the above-described lines are additionally connected by lines which are drawn along the longitudinal muscles. It is also possible for only the lines of the longitudinal muscles to be used to refine the registration, which lines are correspondingly compared for similarity in the regions and their close vicinities which correspond as a result of the approximate registration. However, the comparison of the entire line structures, i.e. the fold lines and the longitudinal muscle lines, between the corresponding regions of the two image data records is particularly advantageous for refining the approximate registration therewith.

The detailed registration based on folds and/or longitudinal muscles is advantageously performed on the basis of an illustration of the intestine from the outside or inside, obtained by a rendering technique, in which the folds and the longitudinal muscles are recognizable.

At least one embodiment of the proposed method can be implemented by way of software and be executed on a computer. At least one embodiment of the corresponding apparatus accordingly can comprise a computational unit with data storage for the volume data records and a registration module designed to carry out the method steps. The volume data records can then be displayed on an image display unit via an appropriate display module. Here it is advantageous if, when the user is navigating in one intestinal region of the one volume data record, the same intestinal region in the other volume data record, determined on the basis of the registration, is likewise displayed on the monitor for the user, either simultaneously or following an appropriate input. This is automatically effected on the basis of the registration.

The detailed registration in the above refinements can be effected in a completely automated fashion by the registration module and the computational unit. A semi-automatic registration supported by the user or manual registration on the basis of displayed image sections is also possible.

BRIEF DESCRIPTION OF THE DRAWINGS

The proposed method and the associated apparatus are again explained briefly in the following text on the basis of example embodiments in connection with the drawings, in which FIG. 3 shows an example of the profile of folds and longitudinal muscles in an intestinal section and FIG. 4 shows a schematic illustration of the proposed apparatus.

DETAILED DESCRIPTION OF THE EXAMPLE EMBODIMENTS

Figure 1:
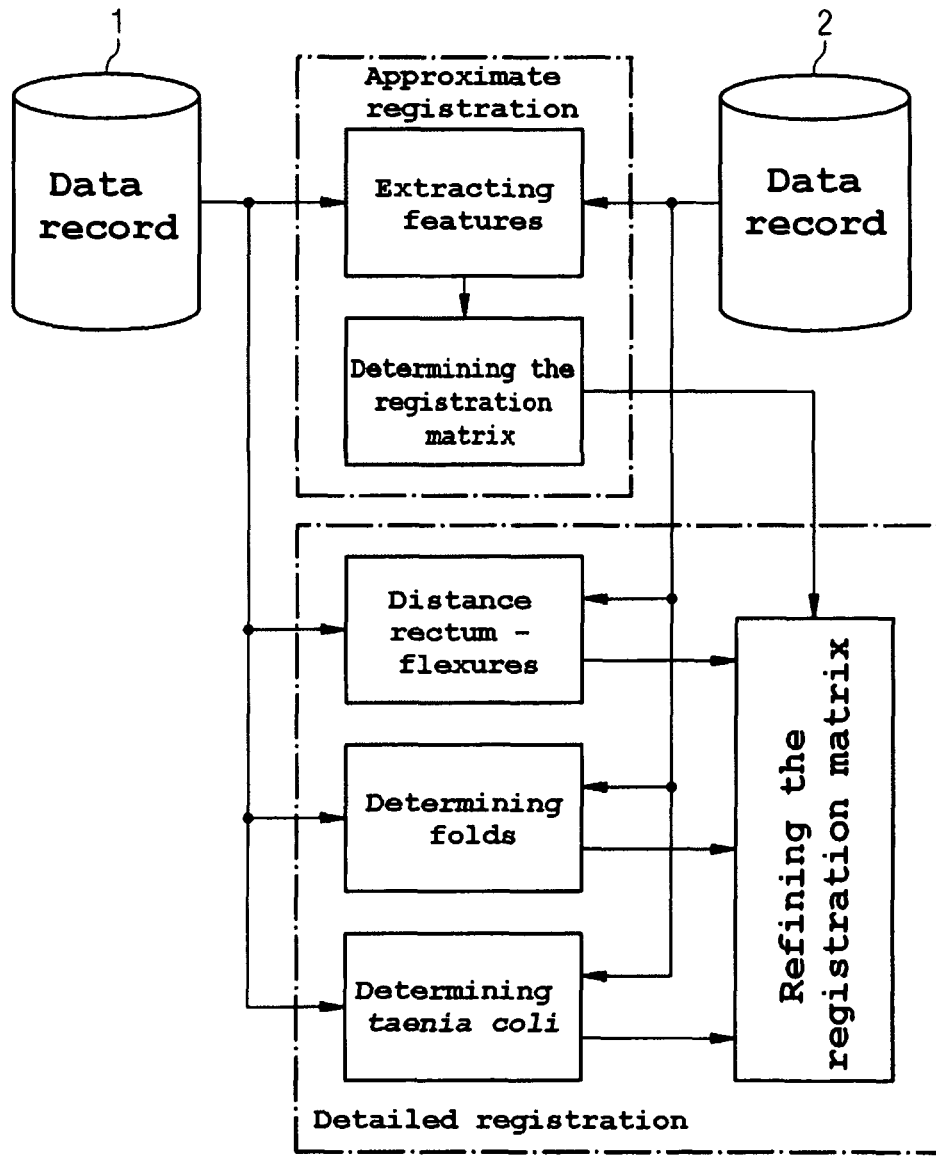
FIG. 1 shows a schematic illustration of an example procedure of the proposed method.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An example procedure of the proposed method is explained on the basis of the schematic illustration of FIG. 1. Here registration of two intestine data records, volume data record 1 and volume data record 2, is intended to be performed with higher precision than has been possible until now using known systems from the prior art. In the method, an approximate registration of the two image data records is firstly performed using known algorithms from the prior art. In the approximate registration, features are extracted on the basis of central lines which reproduce the profile of the intestine in the two image data records. Here similar sections of the intestinal profile are sought after and then assigned to one another. A provisional registration matrix is then obtained from this approximate registration and is subsequently still refined using a detailed registration.

Figure 2:
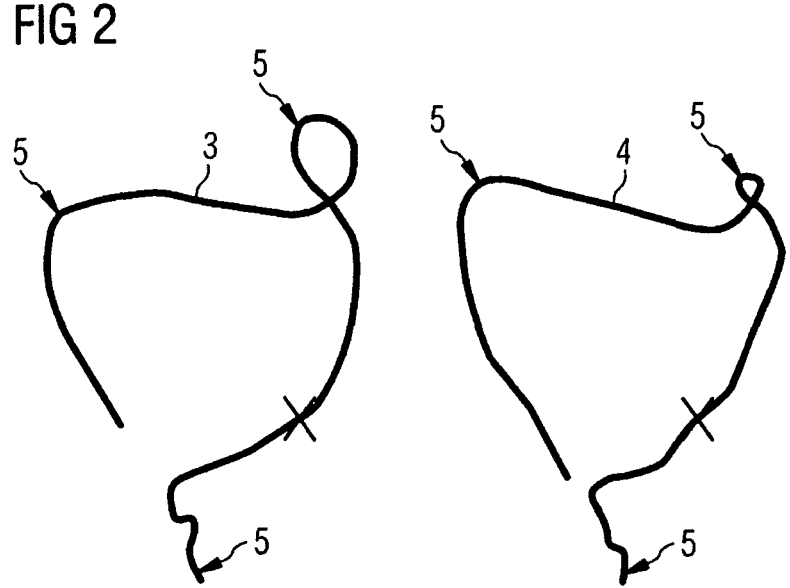
FIG. 2 shows an example of the profile of the central lines in different positions of the patient.

FIG. 2 shows the central lines 3, 4 of the two volume data records of the patient in the prone position (left) and the dorsal position (right). The different profile of the two central lines in the prone position 3 and the dorsal position 4 can be recognized in the figure and said profile causes the inaccuracies in the provisional registration matrix obtained from the approximate registration. The positions of the intestinal profile indicated by arrows which correspond to the three fixed points 5 of the intestine are conspicuous, specifically the rectum (bottom) and the two flexures (top). In one variant of the proposed detailed registration, the distance of individual intestinal sections along the respective intestinal profile from one or more fixed points 5 is used to refine the registration. Thus, by way of example, the point X marks a lesion found in the prone position (left). The lesion is sought after in the dorsal position (right). Due to the repositioning of the intestine between prone and dorsal positions, the approximate registration only finds the lesion by approximation. From the distance of the lesion to the rectum and the left flexure (top right in the image) along the illustrated central line, the exact position can also be found in the dorsal position (right), i.e. in the corresponding volume data record, and the registration matrix can be refined for this intestinal section.

A further option for detailed registration, which can be effected in addition to the above-described distance determination or as an alternative thereto, consists of using folds and/or longitudinal muscles in the intestine. Folds of a different size and shape can be recognized in the large intestine. This can be seen in FIG. 3 which shows a visualization of an intestinal section 13 from the outside obtained by volume rendering. In the longitudinal direction, these folds are interrupted by the so-called "taenia coli", specifically muscles in the longitudinal direction of the intestine. Both the folds and the longitudinal muscles can be used for refining the registration. To this end the vertices of the folds are determined in the respective volume data records and in the intestinal sections 13 and are connected to each other by lines 6 via the valleys caused by the muscles. The central points of the valleys of different folds image the three longitudinal muscles, along which the lines 7 are drawn.

The refinement of the registration can be based on the following different criteria:

Folds of a similar size and shape are respectively sought after in the two volume data records in the vicinity of the intestinal sections 13 assigned by the approximate registration. The approximate registration is then adjusted from equivalent shapes or points.

Figure 3:
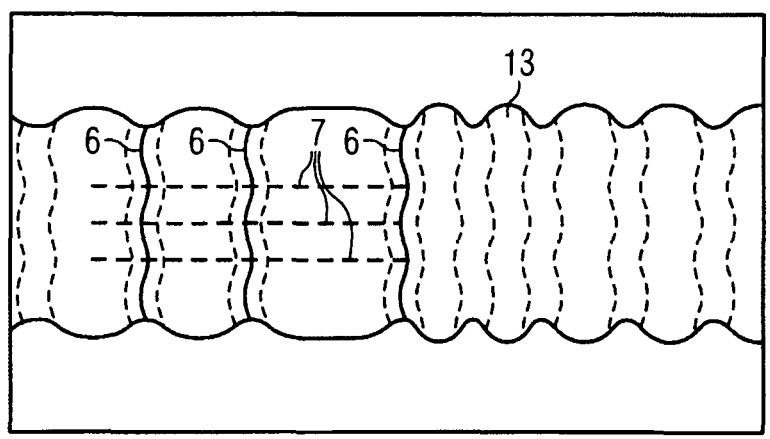

The vertices of the folds are determined in the two image data records in the vicinity of the intestinal sections 13 assigned by the approximate registration and connected to each other by lines 6 via the valleys (cf. FIG. 3). Similar curves then relate to equivalent folds and are used for detailed registration.

The vertices of the folds are determined in the two image data records in the vicinity of the intestinal sections 13 assigned by the approximate registration and connected to each other by lines 6 via the valleys. The central points of the connecting pieces over the valleys of different folds are connected to each other via additional lines 7 (see FIG. 3). The at most three additional lines 7 in each of the prone and dorsal positions, possibly including the distance from the fixed points 5 described above, are then used to determine the detailed registration.

It goes without saying that different combinations of these techniques for detailed registration can be applied.

An apparatus with a computational unit 8, data storage 9 and a registration module 10, in which the described method steps are implemented by way of software, enables the user to quickly switch between the two data records and navigate precisely to the respectively corresponding positions. Such an apparatus is illustrated very schematically in FIG. 4. The individual intestinal sections can be displayed on image display equipment 12 via a display module 11.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for registering at least two volume data records of the intestine which were recorded in two different positions of a patient using a tomographic imaging method, the method comprising:

generating a registration matrix which assigns to each voxel illustrating the intestine, in one volume data record of the at least two volume data records, a corresponding voxel in another volume data record of the at least two volume data records intended to represent a same location in the intestine, the generating including performing an approximate registration in which an intestinal profile is respectively determined for the at least two volume data records, registering the at least two volume data records on the basis of similarities between the two intestinal profiles, and subsequently performing a detailed registration on the at least two volume data records in which the approximate registration is refined on the basis of local anatomical features in the intestine so as to generate the registration matrix for the at least two volume data records.

2. The method as claimed in claim 1, wherein the local anatomical features or a subset thereof are fixed points of the intestine which are localized and assigned in the volume data records and wherein same sections of the intestine in the at least two volume data records are determined and assigned on the basis of the determined distance of said sections along the intestinal profile from the fixed points so as to refine the registration.

3. The method as claimed in claim 1, wherein the local anatomical features or a subset thereof are at least one of folds and longitudinal muscles of the intestine, wherein at least one of folds and longitudinal muscles of similar size and shape are sought after in the at least two volume data records for individual or all intestinal sections in the regions of the intestine respectively assigned by the approximate registration, and wherein the registration is refined on the basis of discovered at least one of folds and longitudinal muscles of similar size and shape.

4. The method as claimed in claim 1, wherein the local anatomical features or a subset thereof are folds of the intestine, wherein vertices of folds are determined in the at least two volume data records for individual or all intestinal sections in the regions of the intestine respectively assigned by the approximate registration and connected for each fold by lines which run in the valleys between the vertices caused by longitudinal muscles, and wherein, in each case, lines of a similar shape are sought after and the registration is refined on the basis of discovered lines of a similar shape.

5. The method as claimed in claim 1, wherein the local anatomical features or a subset thereof are folds and longitudinal muscles of the intestine, wherein vertices of folds are determined in the at least two volume data records for individual or all intestinal sections in the regions of the intestine respectively assigned by the approximate registration and connected for each fold by first lines which run in the valleys between the vertices caused by the longitudinal muscles, wherein the first lines are connected by second lines which follow the longitudinal muscles, and wherein in each case, second lines or a pattern of second and first lines of a similar shape are sought after and the approximate registration is refined on the basis of discovered second lines of a similar shape or on the basis of a discovered pattern of second and first lines of a similar shape.

6. The method as claimed in claim 1, wherein, when an intestinal section, on the basis of the one of the at least two volume data records, is visualized for a user, the same intestinal section, automatically determined from the registration matrix on the basis of the other of the at least two volume data records, is in each case visualized automatically or after a request by the user.

7. The method as claimed in claim 2, wherein the local anatomical features or a subset thereof are at least one of folds and longitudinal muscles of the intestine, wherein at least one of folds and longitudinal muscles of similar size and shape are sought after in the at least two volume data records for individual or all intestinal sections in the regions of the intestine respectively assigned by the approximate registration, and wherein the registration is refined on the basis of discovered at least one of folds and longitudinal muscles of similar size and shape.

8. The method as claimed in claim 2, wherein the local anatomical features or a subset thereof are folds of the intestine, wherein vertices of folds are determined in the at least two volume data records for individual or all intestinal sections in the regions of the intestine respectively assigned by the approximate registration and connected for each fold by lines which run in the valleys between the vertices caused by longitudinal muscles, and wherein, in each case, lines of a similar shape are sought after and the registration is refined on the basis of discovered lines of a similar shape.

9. The method as claimed in claim 2, wherein the local anatomical features or a subset thereof are folds and longitudinal muscles of the intestine, wherein vertices of folds are determined in the at least two volume data records for individual or all intestinal sections in the regions of the intestine respectively assigned by the approximate registration and connected for each fold by first lines which run in the valleys between the vertices caused by the longitudinal muscles, wherein the first lines are connected by second lines which follow the longitudinal muscles, and wherein in each case, second lines or a pattern of second and first lines of a similar shape are sought after and the approximate registration is refined on the basis of discovered second lines of a similar shape or on the basis of a discovered pattern of second and first lines of a similar shape.

10. The method as claimed in claim 2, wherein, when an intestinal section, on the basis of the one of the at least two volume data records, is visualized for a user, the same intestinal section, automatically determined from the registration matrix on the basis of the other of the at least two volume data records, is in each case visualized automatically or after a request by the user.

11. An apparatus for registering at least two volume data records of the intestine which were recorded in two different positions of a patient using a tomographic imaging method, the apparatus comprising:
   a computational unit;
   data storage; and
   a registration module to generate a registration matrix which assigns to each voxel illustrating the intestine, in one volume data record of the at least two volume data records, a corresponding voxel in another volume data record of the at least two volume data records which is intended to represent the same location in the intestine, wherein the registration module is designed to firstly perform an approximate registration in which an intestinal profile is respectively determined for the at least two volume data records and the at least two volume data records are registered on the basis of similarities between the two intestinal profiles and the registration module subsequently is designed to perform a detailed registration on the at least two volume data records in which the approximate registration is refined on the basis of local anatomical features in the intestine so as to generate the registration matrix for the at least two volume data records.

12. The apparatus as claimed in claim 11, wherein the registration module is designed to localize and assign fixed points of the intestine in the at least two volume data records and determine and assign same sections of the intestine in the at least two volume data records on the basis of the determined distance of said sections along the intestinal profile from the fixed points so as to refine the registration.

13. The apparatus as claimed in claim 11, wherein the registration module is designed to, in the at least two volume data records, seek after at least one of folds and longitudinal muscles of similar size and shape for individual or all intestinal sections in the regions of the intestine respectively assigned by the approximate registration, and refine the registration on the basis of discovered at least one of folds and longitudinal muscles of similar size and shape.

14. The apparatus as claimed in claim 11, wherein the registration module is designed to determine vertices of folds in the at least two volume data records for individual or all intestinal sections in the regions of the intestine respectively assigned by the approximate registration and connect them for each fold by lines which run in the valleys between the vertices caused by longitudinal muscles, and subsequently seek after, in each case, lines of a similar shape and refine the registration on the basis of discovered lines of a similar shape.

15. The apparatus as claimed in claim 11, wherein the registration module is designed to determine vertices of folds in the at least two volume data records for individual or all intestinal sections in the regions of the intestine respectively assigned by the approximate registration and connect them for each fold by first lines which run in the valleys between the vertices caused by the longitudinal muscles, connect the first lines by second lines which follow the longitudinal muscles, and subsequently seek after, in each case, second lines or a pattern of second and first lines of a similar shape and refine the approximate registration on the basis of discovered second lines of a similar shape or on the basis of a discovered pattern of second and first lines of a similar shape.

16. The apparatus as claimed in claim 11, further comprising a display module which, when an intestinal section on the basis of one of the at least two volume data records is visualized for a user, automatically or after a request by the user, in each case, is adapted to visualize the same intestinal section automatically determined from the registration matrix on the basis of the other of the at least two volume data records.

17. The apparatus as claimed in claim 12, wherein the registration module is designed to, in the at least two volume data records, seek after at least one of folds and longitudinal muscles of similar size and shape for individual or all intestinal sections in the regions of the intestine respectively assigned by the approximate registration, and refine the registration on the basis of discovered at least one of folds and longitudinal muscles of similar size and shape.

18. The apparatus as claimed in claim 12, wherein the registration module is designed to determine vertices of folds in the at least two volume data records for individual or all intestinal sections in the regions of the intestine respectively assigned by the approximate registration and connect them for each fold by lines which run in the valleys between the vertices caused by longitudinal muscles, and subsequently seek after, in each case, lines of a similar shape and refine the registration on the basis of discovered lines of a similar shape.

19. The apparatus as claimed in claim 12, wherein the registration module is designed to determine vertices of folds in the at least two volume data records for individual or all intestinal sections in the regions of the intestine respectively assigned by the approximate registration and connect them for each fold by first lines which run in the valleys between the vertices caused by the longitudinal muscles, connect the first lines by second lines which follow the longitudinal muscles, and subsequently seek after, in each case, second lines or a pattern of second and first lines of a similar shape and refine the approximate registration on the basis of discovered second lines of a similar shape or on the basis of a discovered pattern of second and first lines of a similar shape.

20. The apparatus as claimed in claim 12, further comprising a display module which, when an intestinal section on the basis of one of the at least two volume data records is visualized for a user, automatically or after a request by the user, in each case, is adapted to visualize the same intestinal section automatically determined from the registration matrix on the basis of the other of the at least two volume data records.

* * * * *